April 3, 1934. M. A. BLAKE Plant Pat. 92
NECTARINE
Filed Nov. 8, 1933
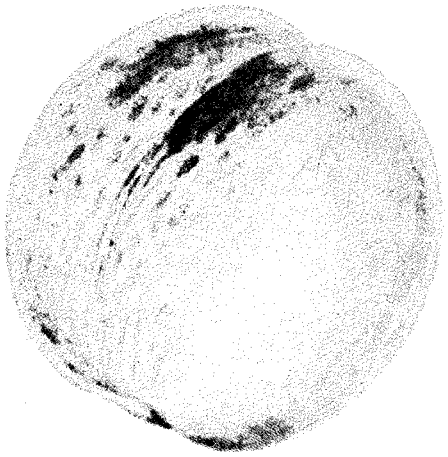
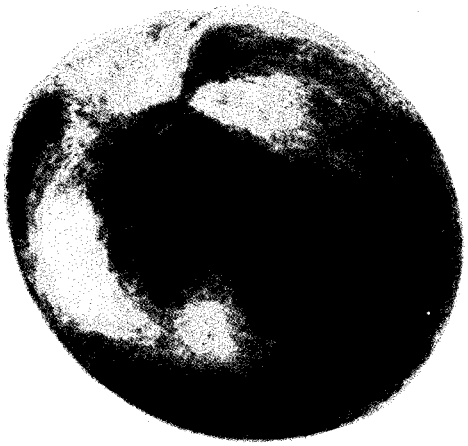
INVENTOR
M.A.Blake
BY Robb & Robb
M. A. Macdonald
Attorneys Patented Apr. 3, 1934

UNITED STATES PATENT OFFICE

92

NECTARINE

Maurice A. Blake, New Brunswick, N. J., assignor to New Jersey State Agricultural Experiment Station, New Brunswick, N. J.

Application November 8, 1933, Serial No. 697,205

1 Claim. (Cl. 47—62)

The present invention relates to a new variety of nectarine, primary characterized as to novelty by the unusual size, form, color and quality of its fruit.

This new variety is the result of the following development: A quantity of peach pits of the variety of Elberta were discarded upon the border of a garden and several of these developed into trees which matured fruits. All of them except one tree produced yellow-fleshed fruits greatly resembling the well known variety Elberta. The other tree produced oval, yellow-fleshed nectarines. Buds from this mutation were employed to propagate the variety upon certain experimental grounds in the State of New Jersey where it was fruited for several years. Then pits of this variety, which had developed as a result of open pollination, germinated and a number of the seedlings were selected and planted out in orchard form. One of the seedlings produced much larger and more round fruit than the original parent. This offspring represents the new variety of plant of this application and it, in turn, has been asexually propagated by "budding" with a resulting reproduction true to form. These reproductions are now full bearing trees with a height of about fourteen feet and a spread of about sixteen feet.

By way of a further specific description it may be noted that the tree has a vigorous, medium spreading habit and sets fruit buds quite freely. Its leaves are large, slightly crinkled with crenate margins and reniform glands. The blades of the leaves are a dark yellowish green and the midribs are of a lighter yellowish green.

The bloom is of the large, showy petalled type, of a light pink color and self fertile.

In the drawing annexed hereto are shown reverse views of two specimens of the fruit of this new plant variety. It will be observed that in form they are round oval. Just before maturity the form tends to be somewhat oval but if the specimens remain upon the tree until soft ripe and the cheeks fill out well, they may appear quite round. The fruit is exceptionally large in size, much larger in fact than any other of the well known varieties including "Lippiatt's Late Orange", "Diamond Jubilee", "Hunter" and many others. It is about one-third larger than a typical specimen of "Goldmine" and many of the specimens measure fully two and one-half inches in length and almost the same in the maximum diameter.

When the fruit is mature the ground color is a greenish yellow becoming a canary yellow when fully soft ripe. The ground color is almost completely overspread with an attractive red, except in the basin and where twigs or leaves shade the fruit, in which case the greenish yellow to lemon yellow ground color prevails. Dull red splashings of color streak the fruit where exposed to light as the specimen begins to acquire its final coloring. In highly colored specimens the dark splashings are more or less obscured by the deep red color of the exposed surface of the fruit.

The flesh of the fruit is yellow with a slight amount of red surrounding the pit. The flesh does not adhere to the pit when the fruit is ripe. It is, in other words, a freestone. The flesh is firm, juicy and of high edible quality.

The fruit ripens in the vicinity of New Brunswick, New Jersey, according to present observations about August 21 to 30.

The foregoing distinctions as regards the fruit serve to distinguish this variety from all other named or cultivated yellow-fleshed varieties. The large leaves with crenate margins and reniform glands together with the large petalled flowers also serve as distinguishing characteristics.

I claim:—

A new and distinct variety of nectarine tree of the type producing yellow-fleshed freestone fruit characterized by the firm, juicy and high edible quality of its fruit as described, and the particular coloring of said fruit composed of an attractive red coloring upon a yellow back ground marked by dull red splashes where not obscured by the brighter red color of the fully exposed parts of the surface, as shown.

MAURICE A. BLAKE.